United States Patent [19]

Garth

[11] 4,413,619

[45] Nov. 8, 1983

[54] PORTABLE CERVICAL COLLAR

[76] Inventor: Geoffrey C. Garth, 334 Colorado Pl., Long Beach, Calif. 90814

[21] Appl. No.: 311,959

[22] Filed: Oct. 16, 1981

[51] Int. Cl.³ .............................................. A61F 5/08
[52] U.S. Cl. .................... 128/76 R; 128/87 B
[58] Field of Search .................. 128/132 R, DIG. 23, 128/76 R, 83, 75, 87 R, 87 B, 88, 89 R, 89 A

[56] References Cited

U.S. PATENT DOCUMENTS

| | | | |
|---|---|---|---|
| 3,024,784 | 3/1962 | Monfardini | 128/87 R |
| 3,306,284 | 2/1967 | McKinley | 128/75 |
| 3,313,297 | 4/1967 | Applegate | 128/75 |
| 3,504,667 | 4/1970 | McFarlane | 128/87 R |
| 3,530,853 | 9/1970 | Bond | 128/87 B |
| 4,041,940 | 8/1977 | Frankel et al. | 128/87 R |

Primary Examiner—Richard J. Apley
Assistant Examiner—David J. Isabella
Attorney, Agent, or Firm—Fischer, Tachner & Strauss

[57] ABSTRACT

There is disclosed a portable cervical collar formed of an elongated band of stiff, flexible sheet material which can be formed into a cylindrical collar. The collar includes a chin support brace which is a generally C-shaped flat sheet that can be attached with its opposite ends secured to opposite sides of the formed collar thereby forming a concave, forwardly projecting support shelf to immobilize the wearer's chin. The collar is intended as a portable, compact collar for field use by paramedics and the like during transportation and initial examination of a patient.

10 Claims, 6 Drawing Figures

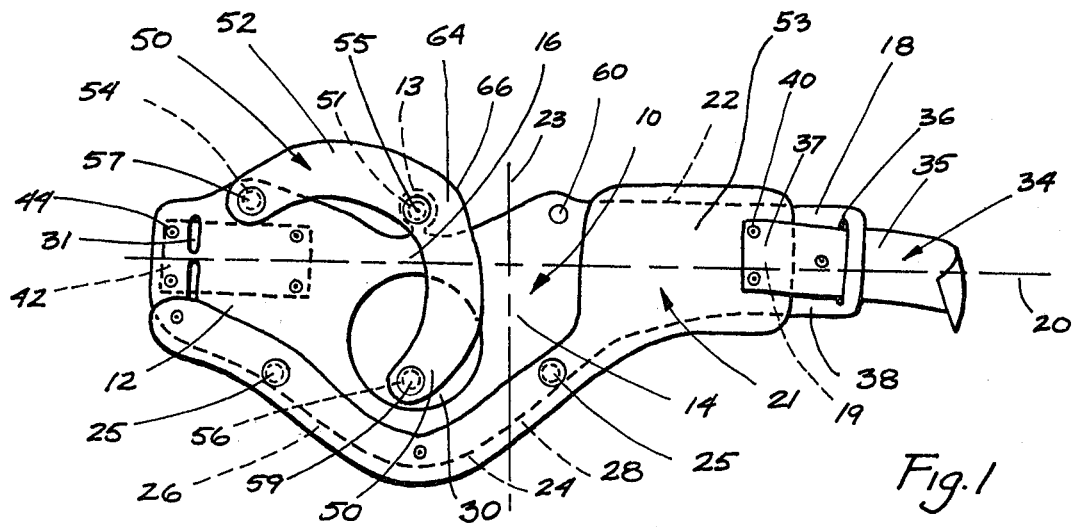

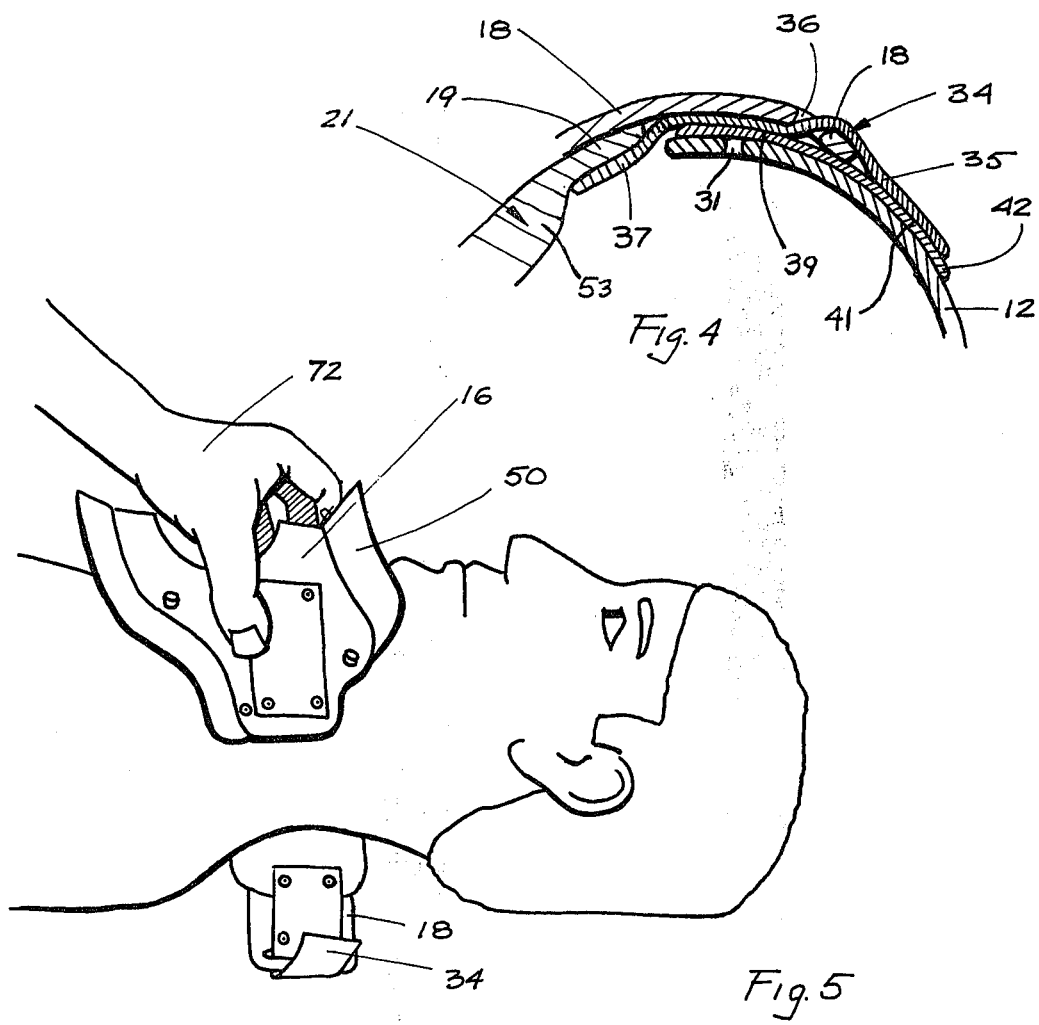
Fig. 4
Fig. 5
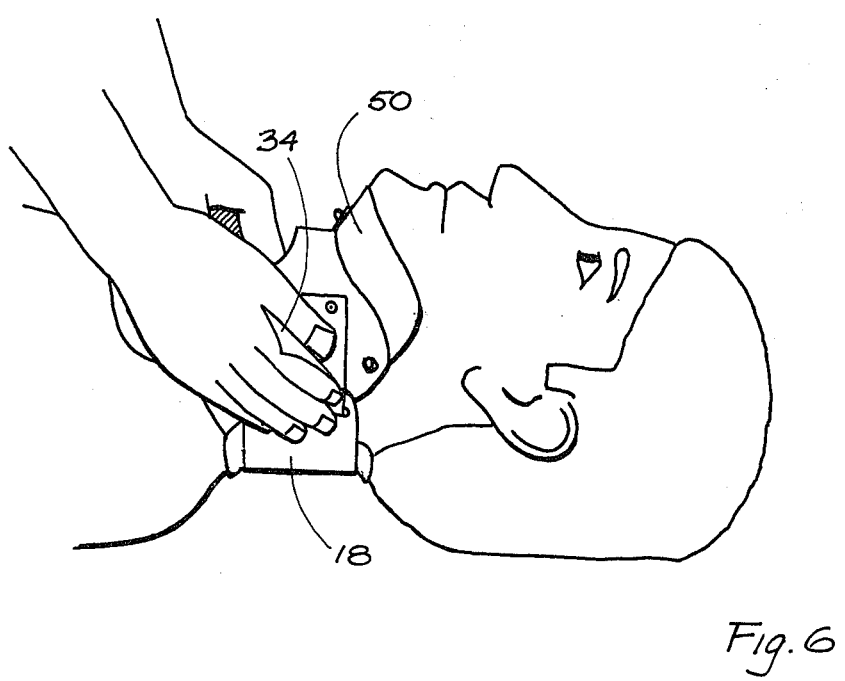
Fig. 6

PORTABLE CERVICAL COLLAR

BACKGROUND OF THE INVENTION

Cervical collars are commonly formed of relatively thick material, usually in two pieces which are assembled about a wearer's neck. These collars are too bulky and cumbersome for field use by paramedics. Some attempts have been made to provide cervical collars from stiff flexible sheet material which is cut into an elongated band that is encircled about the wearer's neck. Although rolled edges of leather or plastic foam have been provided on some of these collars as in U.S. Pat. No. 3,075,521, none of these cervical collars adequately provide support and restraint for the wearer's chin. A chin restraint is desirable and usually essential to immobilize the patient's neck and prevent movement during transporting and preliminary examining of the patient.

BRIEF STATEMENT OF THE INVENTION

This invention comprises a portable cervical collar which has a chin brace to immoblize a patient's chin and neck. The collar is formed of an elongated band of stiff, flexible material such as various plastics. A chin support brace is provided in the form of a generally C-shaped plate which can be secured at its opposite ends to opposite sides of the cervial collar. The central or bight portion of the chin support, when assembled to the formed collar, projects forward from the front of the collar and forms an upwardly inclined, conically convex support or rest for the patient's chin. In the preferred embodiment, the neck encircling elongated band is secured in its formed collar configuration by Velcro fasteners which attach at one side of the collar.

BRIEF DESCRIPTION OF THE DRAWINGS

The invention will be described with reference to the figures of which:

FIG. 1 illustrates the cervial collar of the invention in its flat, unassembled position;

FIG. 2 illustrates the collar of the invention partially assembled;

FIG. 3 illustrates the cervical collar of the invention assembled on a patient; and FIG. 4 is a view along lines 4—4 of FIG. 3; and FIGS. 5 and 6 illustrate the application of the cervical collar of the invention.

BRIEF DESCRIPTION OF THE INVENTION

The cervical collar of the invention is shown in FIG. 1 in its unassembled or portable configuration as it would be carried by paramedics in a portable pack or a mobile paramedic unit. The collar comprises an elongated band 10 which is formed of a stiff flexible sheet material such as various plastics, e.g., high and low density polyethylene, polyvinylchloride, acrylonitrile-butadiene-styrene copolymer, polypropylene, etc. The elongated band 10 has two side portions 12 and 14, an intermediate front portion 16 and a back portion 18. The front portion 16 is of greater width than the side portions 12 and 14 and is laterally transposed a substantial distance from the longitudinal axis 20 of band 10. The opposite longitudinal edges 22 and 24 of band 10 are curvilinear with smooth transitions such as 26 and 28 between the side and forward portions. A foam strip 21 is preferably secured to the lower edge 24 of the band 10 by suitable fastening means, e.g., snap fasteners and/or staples. Cement or other bonding means can also be used. Preferably the foam strip 21 includes a foam pad 53 overlying the inside surface of back 18, as shown. This provides additional comfort to the patient. The attachment band 34 is applied over the inside surface of the pad 51 to permit assembly as shown in FIGS. 3 and 4. The attachment band 34 overlies a short portion 19 of foam pad 53, as shown in FIG. 4. Similarly, the entire inside surface of the chin support brace 50 can receive a cushioning pad. The pads which are used can be foamed plastics such as polyurethane. Most preferably, the foam strip projects a slight distance past the lower edge 24, as shown to provide maximum cushioning to the patient.

A large aperture 30 is preferably provided centrally located in the forward portion to provide access to the patient's throat for an emergency tracheostomy. The hole is optional and may be left out, particularly when the collar is formed of materials having lesser rigidity such as low density polyethylene.

In its preferred embodiment, the elongated band 10 is asymmetric about its lateral axis 23 with the back portion 18 of band 10 being integral with one side portion 14, thereby providing the band retaining means to the side of the formed collar, in a manner hereinafter described. The back portion 18 is preferably of reduced width, substantially as shown, and distally carries the collar retaining means, attachment or assembly band 34. The elongated band 10 has a laterally transverse slot 36 adjacent one end, and the attachment or retaining band 34 is passed through this slot, from the inside wall 38 of band 10 and has a free or unattached end portion 35 of approximately equal length to its attached end portion 37. The attachment band, which preferably is a Velcro fastener, is secured to the elongated band 10 by any suitable means such as rivets 40 and other fasteners.

A cooperative Velcro attachment band 42 is secured to the outside wall of the opposite side portion 12, again with suitable fasteners such as rivets 44 and the like.

The chin support brace 50 is a generally C-shaped plate 52 which has distal apertures 54 and 56 and a central aperture 51. Preferably, one end of plate 52 is permanently secured to one of the sides 12 of the collar by suitable means, e.g., a rivet or snap fastener 57. The center of chin support brace 50 is also secured to the collar by snap fastener 55 which extends through aperture 51 and into an aligned aperture of apendage or tab 13 that projects from edge 22 of the collar. The opposite end of the plate 52 is unattached, however suitable attachment means such as a snap fastener 59 is provided whereby the opposite or free end 58 of plate 52 can be secured to the opposite side 14 of the elongated band 10 during assembly of the cervical collar. To this end, a cooperative aperture 60 is provided at a symmetrical position in side 14 relative to the front portion 16 of band 10.

The chin support brace 50, as previously mentioned, has a general C-shape with bight portion 64 of expanded width with an arcuate forward edge 66. Chin support 50 can be formed of the same, stiff, flexible sheet material as used for elongated band 10, or if desired a sheet material of a preselected stiffness, e.g., one having slightly more pliability, can be used for greater patient comfort while still providing the necessary immobilization.

Referring now to FIG. 2, the assembly of the cervical collar will be described. As shown in FIG. 2, the cervical collar is partially assembled; with the chin support brace 50 secured with both of its ends attached to the opposite sides 12 and 14 of the collar 10. This is accomplished by bowing the front portion 16 and moving the chin support brace to align apertures 56 and 60 and then securing the assembly by inserting the snap fastener 59 through the aligned apertures. Additionally, the attachment of the chin support brace to the opposite sides of the cervical collar in the illustrated manner reinforces the cervical collar and retains it in a partially cylindrical configuration with an arcuate bow 70 to the front portion 16 of the collar 10. In this configuration, the cervical collar is ready for application on the patient.

FIG. 3 shows the cervical collar in place about a patient's neck 74. The collar is secured in assembly by engagement of band 34 with its cooperative band 42. In this position, the chin support brace 50 firmly supports the patients' chin 76.

As shown in FIG. 4, the attachment band 34 cooperatively engages the cooperative band 42 at two locations; 39 and 41. Generally, the first engagement area 39 is sufficient to retain the assembly, however, a more secure assembly is insured by the engagement area 41 between the end portion 35, which overlies the end 18 of band 10, and the cooperative band 42. This insures that the resiliency of the plastic band 10 does not spring the assembly apart. Assembly is also enhanced by the slots 31 (see FIG. 1) which slightly weaken the end of the collar and permit its deflection before application.

Referring now to FIGS. 5 and 6, there is illustrated the application of the cervical collar to a patient in the supine position. The cervical collar can be readily applied by a paramedic holding the bowed forward portion 16 in one hand 72 while slipping the back portion 18 beneath the patient's neck. The collar can then be guided into place to firmly seat beneath the patient's chin. The back portion is wrapped about the patient's neck, joining the collar into its assembled position with the fabric attachment band 34 secured to its cooperative band 42 on the outside of side portion 12 of the collar 10.

The cervical collar as thus described is ideally suited for portable or field use by paramedics. Because the entire collar can be unfolded into a flat position, it can be packed in a portable medical supply kit or stored in a mobile paramedic unit. The chin support brace is preferably attached with one end permanently secured in a pivot attachment to the collar so that it is always present when needed in an emergency. The collar can be readily applied by a single paramedic since the assembly of the chin support brace to both sides of the collar preforms the forward portion of the collar, imparting a bowed configuration thereto, thereby permitting placement of the forward and side portions of the collar about the patient's neck with a single handed operation. Since the collar is asymmetric about its lateral axis with the back portion integral with one side portion, the collar can be readily applied to supine patients since the collar is assembled at the side rather than at the back.

The cervical collar is intended primarily for temporary use in transporting and preliminary examination of the patient. The collar is formed entirely of plastic or similar material which is transparent to X-rays, thereby permitting X-ray examination of the patient wearing the collar. The large aperture in the front portion of the collar permits insertion of a tube and/or permits paramedics to perform tracheostomies with the collar in place. Throughout all transporting and examining of the patient, the patient's chin is maintained in an immobilized condition under a slight upward pressure from the chin support brace, all as desired for safe and correct treatment.

The invention has been described with reference to the illustrated and presently preferred embodiment. It is not intended that the invention be limited by this description of preferred embodiments. Instead, it is intended that the invention be defined by the means, and the obvious equivalents, set forth in the following claims.

What is claimed is:

1. A cervical collar formed entirely of a stiff, flexible flat plastic sheet band having an assymetrical configuration comprising:
   (a) an elongated neck encircling band formed of said stiff, flexible sheet material having front, side and back portions;
   (b) a chin support brace, also formed entirely of stiff flexible plastic sheet material having a generally C-shape including fastening means located on each end of said brace;
   (c) said chin support brace fastening means being engageable with cooperative attachment means located at least on opposite sides of said neck encircling band such that when said band is formed into said collar at least one of said fastening means is allowed to align with a respective attachment means thus bowing said brace thereby enabling said brace to obtain an upwardly inclined, conically convex chin rest supported along its' entire length by the upper edge of the front portion of said band and projecting forwardly therefrom;
   (d) collar retention means carried at each end of said band and mutually cooperative to retain said band in its collar configuration.

2. The cervical collar of claim 1 wherein said front portion of said band is laterally offset from, and of greater width than, said side portions with curvilinear edges with smooth transition therebetween.

3. The cervical collar of claim 2 wherein said back portion of said band is of lesser width than said side portions.

4. A cervical collar formed of a stiff, flexible plastic sheet band having an assymitrical configuration comprising:
   (a) an elongated neck encircling band formed of stiff, flexible sheet material having a front, side and back portions with said back portion integral with one of said side portions whereby said band is joined together to form said collar at one side thereof;
   (b) a chin support brace, also formed entirely of stiff flexible plastic sheet material having a generally C-shape including fastening means located on each end of said brace;
   (c) said chin support brace fastening means being engageable with cooperative attachment means located at least on opposite sides of said neck encircling band such that when said band is formed into said collar at least one of said fastening means is allowed to align with a respective attachment means thus bowing said brace thereby enabling said brace to obtain an upwardly inclined, conically convex chin rest supported along its' entire length by the upper edge of the front portion of said band and projecting forwardly therefrom;
   (d) collar retention means, one each carried at the side end and at the back end of said band and mutually cooperative to retain said band in its collar configuration.

5. The cervical collar of claim 4 wherein said neck encircling band has a distal slot and secured to the inside wall of said encircling band is a first band of attachment fabric extending through said slot and having a free end extending past and overlying the end of said encircling band, and the opposite end of said neck encircling band has a coacting second band of attachment fabric secured to its outside wall to underlie said first band of attachment fabric when said neck encircling band is folded into said collar.

6. The cervical collar of claim 5 wherein said band of attachment fabric is engageable by a cooperative attachment fabric carried on the outside surface of one side portion of said encircling band.

7. The cervical collar of claim 1 wherein the bight portion of said chin support brace is of greater width than the remainder of said brace.

8. The cervical collar of claim 5 wherein one end of said chin support brace is permanently secured to one side of said neck encircling band and includes detachable means for connecting its opposite end to the opposite side of said neck encircling band during assembly of said collar whereby said chin support brace can be unfolded into a flat configuration and folded and secured into said conically convex shape.

9. The cervical collar of claim 1 including a resilient band secured along and projecting slightly over the lower edge of said elongated band.

10. The cervical collar of claim 8 including an integral tab centrally dependent from the upper edge of said front portion of said band and permanently attached to the central undersurface of said chin support brace.

* * * * *